(12) United States Patent
Christensen et al.

(10) Patent No.: US 10,307,182 B2
(45) Date of Patent: Jun. 4, 2019

(54) VALVED SHEATH INTRODUCER FOR VENOUS CANNULATION

(71) Applicant: C. R. Bard, Inc., Murray Hill, NJ (US)

(72) Inventors: Mark A. Christensen, Salt Lake City, UT (US); Steven M. Smith, Sandy, UT (US); Walter H. Shang, Irvine, CA (US); James D. Beal, South Jordan, UT (US)

(73) Assignee: C. R. Bard, Inc., Murray Hill, NJ (US)

( * ) Notice: Subject to any disclaimer, the term of this patent is extended or adjusted under 35 U.S.C. 154(b) by 672 days.

(21) Appl. No.: 14/749,514

(22) Filed: Jun. 24, 2015

(65) Prior Publication Data

US 2015/0289903 A1 Oct. 15, 2015

Related U.S. Application Data

(62) Division of application No. 12/648,533, filed on Dec. 29, 2009, now Pat. No. 9,108,033, which is a division
(Continued)

(51) Int. Cl.
*A61B 17/34* (2006.01)
*A61M 39/06* (2006.01)
*A61M 25/06* (2006.01)

(52) U.S. Cl.
CPC ...... *A61B 17/3415* (2013.01); *A61B 17/3498* (2013.01); *A61M 39/0693* (2013.01);
(Continued)

(58) Field of Classification Search
CPC .. A61M 39/04; A61M 39/06; A61M 39/0606; A61M 39/0613;
(Continued)

(56) References Cited

U.S. PATENT DOCUMENTS 675,157 A 5/1901 Howard
2,908,283 A 10/1959 Kiffer et al.
(Continued)

FOREIGN PATENT DOCUMENTS

CN 103260694 A 8/2013
EP 0370721 A2 5/1990
(Continued)

OTHER PUBLICATIONS

US 5,520,663 A, 05/1996, Patterson et al. (withdrawn)
(Continued)

*Primary Examiner* — Quynh-Nhu H. Vu
(74) *Attorney, Agent, or Firm* — Rutan & Tucker, LLP

(57) ABSTRACT

A valved sheath introducer for venous cannulation, including a valve, sheath, handle and cap. The valve is configured to permit safe introduction and removal of medical instruments through the sheath introducer. The valve may have one or more anchoring members and a thickened central portion through which a slit is formed. The central portion may have one or more concave surfaces and the slit can be angled with respect to the top surface of the valve. The cap is attached to the handle, compressing a portion of the valve therebetween.

14 Claims, 9 Drawing Sheets

Related U.S. Application Data of application No. 11/119,599, filed on May 2, 2005, now Pat. No. 7,637,893.

(60) Provisional application No. 60/566,896, filed on Apr. 30, 2004.

(52) U.S. Cl.
CPC .... *A61M 25/0662* (2013.01); *Y10T 29/49405* (2015.01); *Y10T 29/49412* (2015.01); *Y10T 29/49826* (2015.01); *Y10T 137/788* (2015.04); *Y10T 137/7885* (2015.04)

(58) Field of Classification Search
CPC .... A61M 2039/062; A61M 2039/0626; A61M 2039/0633; A61M 2039/0673; A61M 39/0693; Y10T 137/788; Y10T 137/7885; Y10T 29/49405; Y10T 29/49412; Y10T 29/49826; A61B 17/3415; A61B 17/3498
See application file for complete search history.

(56) References Cited

U.S. PATENT DOCUMENTS

| | | | |
|---|---|---|---|
| 2,912,981 A | 11/1959 | Keough | |
| 3,176,690 A | 4/1965 | H'Doubler | |
| D217,795 S | 6/1970 | Spaven | |
| 3,612,050 A | 10/1971 | Sheridan | |
| 3,805,794 A | 4/1974 | Schlesinger | |
| 3,853,127 A | 12/1974 | Spademan | |
| 4,000,739 A | 1/1977 | Stevens | |
| 4,068,659 A | 1/1978 | Moorehead | |
| 4,089,506 A | 5/1978 | Blake | |
| 4,143,853 A | 3/1979 | Abramson | |
| 4,198,973 A | 4/1980 | Millet | |
| 4,233,974 A | 11/1980 | Desecki et al. | |
| 4,296,747 A | 10/1981 | Ogle | |
| 4,306,562 A | 12/1981 | Osborne | |
| 4,354,491 A | 10/1982 | Marbry | |
| 4,387,879 A | 6/1983 | Tauschinski | |
| 4,411,654 A | 10/1983 | Boarini et al. | |
| 4,412,832 A | 11/1983 | Kling et al. | |
| 4,424,833 A * | 1/1984 | Spector | A61M 39/0606 128/202.15 |
| 4,430,081 A | 2/1984 | Timmermans | |
| 4,431,426 A | 2/1984 | Groshong et al. | |
| 4,436,519 A | 3/1984 | O'Neill | |
| 4,445,893 A | 5/1984 | Bodicky | |
| 4,449,973 A | 5/1984 | Luther | |
| 4,453,928 A | 6/1984 | Steiger | |
| 4,468,224 A | 8/1984 | Enzmann et al. | |
| 4,473,067 A | 9/1984 | Schiff | |
| RE31,855 E | 3/1985 | Osborne | |
| 4,504,269 A | 3/1985 | Durand et al. | |
| 4,557,261 A | 12/1985 | Rugheimer et al. | |
| 4,571,241 A | 2/1986 | Christopher | |
| 4,581,012 A | 4/1986 | Brown et al. | |
| 4,581,025 A | 4/1986 | Timmermans | |
| 4,588,398 A | 5/1986 | Daugherty et al. | |
| 4,591,355 A | 5/1986 | Hilse | |
| 4,596,559 A | 6/1986 | Fleischhacker | |
| 4,610,665 A | 9/1986 | Matsumoto et al. | |
| 4,610,671 A | 9/1986 | Luther | |
| 4,619,643 A | 10/1986 | Bai | |
| 4,626,245 A * | 12/1986 | Weinstein | A61M 39/0606 137/849 |
| 4,634,432 A | 1/1987 | Kocak | |
| 4,650,472 A | 3/1987 | Bates | |
| 4,654,031 A | 3/1987 | Lentz | |
| 4,657,772 A | 4/1987 | Kocak | |
| 4,673,393 A | 6/1987 | Suzuki et al. | |
| 4,701,159 A | 10/1987 | Brown et al. | |
| 4,705,511 A | 11/1987 | Kocak | |
| 4,722,725 A | 2/1988 | Sawyer et al. | |
| 4,723,550 A | 2/1988 | Bales et al. | |
| 4,726,374 A | 2/1988 | Bales et al. | |
| 4,743,265 A | 5/1988 | Whitehouse et al. | |
| 4,747,833 A | 5/1988 | Kousai et al. | |
| 4,748,982 A | 6/1988 | Horzewski et al. | |
| 4,753,765 A | 6/1988 | Pande | |
| 4,772,266 A | 9/1988 | Groshong | |
| 4,784,644 A | 11/1988 | Sawyer et al. | |
| 4,795,426 A | 1/1989 | Jones | |
| 4,798,594 A | 1/1989 | Hillstead | |
| 4,809,679 A | 3/1989 | Shimonaka et al. | |
| 4,842,591 A | 6/1989 | Luther | |
| 4,842,592 A | 6/1989 | Caggiani et al. | |
| 4,865,593 A | 9/1989 | Ogawa et al. | |
| 4,895,565 A | 1/1990 | Hillstead | |
| 4,909,798 A | 3/1990 | Fleischhacker et al. | |
| 4,921,479 A | 5/1990 | Grayzel | |
| 4,929,235 A | 5/1990 | Merry et al. | |
| 4,929,236 A | 5/1990 | Sampson | |
| 4,932,633 A | 6/1990 | Johnson et al. | |
| 4,935,010 A | 6/1990 | Cox et al. | |
| 4,936,826 A | 6/1990 | Amarasinghe | |
| 4,946,133 A | 8/1990 | Johnson et al. | |
| 4,952,359 A | 8/1990 | Wells | |
| 4,956,755 A | 9/1990 | Maglica et al. | |
| 4,960,412 A | 10/1990 | Fink | |
| 4,966,588 A | 10/1990 | Rayman et al. | |
| 4,973,312 A | 11/1990 | Andrew | |
| 4,983,168 A | 1/1991 | Moorehead | |
| 4,994,027 A | 2/1991 | Farrell | |
| 4,997,424 A | 3/1991 | Little | |
| 5,000,745 A | 3/1991 | Guest et al. | |
| 5,007,901 A | 4/1991 | Shields | |
| 5,009,391 A | 4/1991 | Steigerwald | |
| 5,011,478 A | 4/1991 | Cope | |
| 5,035,686 A | 7/1991 | Crittenden et al. | |
| 5,041,095 A | 8/1991 | Littrell | |
| 5,053,014 A | 10/1991 | Van Heugten | |
| 5,064,414 A | 11/1991 | Revane | |
| 5,066,285 A | 11/1991 | Hillstead | |
| 5,071,411 A | 12/1991 | Hillstead | |
| 5,078,688 A | 1/1992 | Lobodzinski et al. | |
| 5,085,645 A | 2/1992 | Purdy et al. | |
| 5,092,857 A | 3/1992 | Fleischhacker | |
| 5,098,392 A | 3/1992 | Fleischhacker et al. | |
| 5,098,393 A | 3/1992 | Amplatz et al. | |
| 5,102,395 A | 4/1992 | Cheer et al. | |
| 5,104,389 A | 4/1992 | Deem et al. | |
| 5,106,054 A | 4/1992 | Mollenauer et al. | |
| 5,112,301 A | 5/1992 | Fenton, Jr. et al. | |
| 5,114,408 A | 5/1992 | Fleischhaker et al. | |
| 5,117,836 A | 6/1992 | Millar | |
| 5,125,903 A | 6/1992 | McLaughlin et al. | |
| 5,125,904 A | 6/1992 | Lee | |
| 5,141,497 A | 8/1992 | Erskine | |
| 5,149,327 A | 9/1992 | Oshiyama et al. | |
| 5,154,701 A | 10/1992 | Cheer et al. | |
| 5,156,596 A | 10/1992 | Balbierz et al. | |
| 5,158,545 A | 10/1992 | Trudell et al. | |
| 5,160,323 A | 11/1992 | Andrew et al. | |
| 5,163,903 A | 11/1992 | Crittenden et al. | |
| 5,167,634 A | 12/1992 | Corrigan, Jr. et al. | |
| 5,167,637 A | 12/1992 | Okada et al. | |
| 5,169,393 A | 12/1992 | Moorehead et al. | |
| 5,171,222 A | 12/1992 | Euteneuer et al. | |
| 5,176,652 A | 1/1993 | Littrell | |
| 5,180,372 A | 1/1993 | Vegoe et al. | |
| 5,188,605 A | 2/1993 | Sleep | |
| 5,190,529 A | 3/1993 | McCrory et al. | |
| 5,191,898 A | 3/1993 | Millar | |
| 5,197,976 A | 3/1993 | Herweck et al. | |
| 5,201,722 A | 4/1993 | Moorehead et al. | |
| 5,205,834 A | 4/1993 | Moorehead et al. | |
| 5,207,649 A | 5/1993 | Aruny | |
| 5,211,633 A | 5/1993 | Stouder, Jr. | |
| 5,215,538 A | 6/1993 | Larkin | |
| 5,221,263 A | 6/1993 | Sinko et al. | |
| 5,224,930 A | 7/1993 | Spaeth et al. | |
| 5,234,407 A | 8/1993 | Teirstein et al. | |

(56) References Cited

U.S. PATENT DOCUMENTS

| | | |
|---|---|---|
| 5,234,410 A | 8/1993 | Graham et al. |
| 5,234,438 A | 8/1993 | Semrad |
| 5,242,413 A | 9/1993 | Heiliger |
| 5,242,430 A | 9/1993 | Arenas et al. |
| 5,242,431 A | 9/1993 | Kristiansen |
| 5,250,033 A | 10/1993 | Evans et al. |
| 5,255,691 A | 10/1993 | Otten |
| 5,269,771 A | 12/1993 | Thomas et al. |
| 5,273,540 A | 12/1993 | Luther et al. |
| 5,273,546 A | 12/1993 | McLaughlin et al. |
| 5,275,583 A | 1/1994 | Crainich |
| 5,279,597 A | 1/1994 | Dassa et al. |
| 5,290,294 A | 3/1994 | Cox et al. |
| 5,292,311 A | 3/1994 | Cope |
| 5,304,142 A | 4/1994 | Liebl et al. |
| 5,304,156 A | 4/1994 | Sylvanowicz et al. |
| 5,306,240 A | 4/1994 | Berry |
| 5,312,355 A * | 5/1994 | Lee .................. A61M 25/0668 604/160 |
| 5,312,357 A | 5/1994 | Buijs et al. |
| 5,318,542 A | 6/1994 | Hirsch et al. |
| 5,320,602 A | 6/1994 | Karpiel |
| 5,324,271 A | 6/1994 | Abiuso et al. |
| 5,334,157 A | 8/1994 | Klein et al. |
| 5,334,187 A | 8/1994 | Fischell et al. |
| 5,336,192 A | 8/1994 | Palestrant |
| 5,348,537 A | 9/1994 | Wiesner et al. |
| 5,350,362 A | 9/1994 | Stouder, Jr. |
| 5,350,363 A | 9/1994 | Goode et al. |
| 5,364,393 A | 11/1994 | Auth et al. |
| 5,368,574 A | 11/1994 | Antonacci et al. |
| 5,382,241 A | 1/1995 | Choudhury et al. |
| 5,389,081 A | 2/1995 | Castro |
| 5,389,090 A | 2/1995 | Fischell et al. |
| 5,391,152 A | 2/1995 | Patterson |
| 5,395,352 A | 3/1995 | Penny |
| 5,397,310 A | 3/1995 | Chu et al. |
| 5,397,311 A | 3/1995 | Walker et al. |
| 5,405,320 A | 4/1995 | Twardowski et al. |
| 5,405,323 A | 4/1995 | Rogers et al. |
| 5,405,329 A | 4/1995 | Durand et al. |
| 5,409,463 A | 4/1995 | Thomas et al. |
| 5,409,464 A | 4/1995 | Villalobos |
| 5,409,469 A | 4/1995 | Schaerf |
| 5,413,561 A | 5/1995 | Fischell et al. |
| 5,419,340 A | 5/1995 | Stevens |
| 5,423,762 A | 6/1995 | Hillstead |
| 5,429,616 A | 7/1995 | Schaffer |
| 5,437,645 A | 8/1995 | Urban et al. |
| 5,441,504 A | 8/1995 | Pohndorf et al. |
| 5,453,095 A | 9/1995 | Davila et al. |
| 5,460,616 A | 10/1995 | Weinstein et al. |
| 5,466,230 A | 11/1995 | Davila |
| 5,472,418 A | 12/1995 | Palestrant |
| 5,472,435 A | 12/1995 | Sutton |
| 5,474,099 A | 12/1995 | Boehmer et al. |
| 5,474,544 A | 12/1995 | Lynn |
| 5,484,401 A | 1/1996 | Rodriguez et al. |
| 5,488,960 A | 2/1996 | Toner |
| 5,489,269 A | 2/1996 | Aldrich et al. |
| 5,489,273 A | 2/1996 | Whitney et al. |
| 5,496,346 A | 3/1996 | Horzewski et al. |
| 5,499,975 A | 3/1996 | Cope et al. |
| 5,501,676 A | 3/1996 | Niedospial et al. |
| 5,509,897 A | 4/1996 | Twardowski et al. |
| 5,520,655 A | 5/1996 | Davila et al. |
| 5,536,255 A | 7/1996 | Moss |
| 5,538,505 A | 7/1996 | Weinstein et al. |
| 5,549,651 A | 8/1996 | Lynn |
| 5,556,387 A | 9/1996 | Mollenauer et al. |
| 5,558,652 A | 9/1996 | Henke |
| 5,599,305 A | 2/1997 | Hermann et al. |
| 5,603,702 A | 2/1997 | Smith et al. |
| 5,613,663 A | 3/1997 | Schmidt et al. |
| 5,613,953 A | 3/1997 | Pohndorf |
| 5,613,956 A | 3/1997 | Patterson et al. |
| 5,647,857 A | 7/1997 | Anderson et al. |
| 5,653,697 A | 8/1997 | Quiachon et al. |
| 5,653,698 A | 8/1997 | Niedospial et al. |
| 5,657,963 A | 8/1997 | Hinchliffe et al. |
| 5,662,606 A | 9/1997 | Cimino et al. |
| 5,672,158 A | 9/1997 | Okada et al. |
| 5,685,856 A | 11/1997 | Lehrer |
| 5,685,858 A | 11/1997 | Kawand |
| 5,702,370 A | 12/1997 | Sylvanowicz et al. |
| 5,713,867 A | 2/1998 | Morris |
| 5,727,770 A | 3/1998 | Dennis |
| 5,735,819 A | 4/1998 | Elliott |
| 5,741,233 A | 4/1998 | Riddle et al. |
| 5,741,234 A | 4/1998 | Aboul-Hosn |
| 5,752,937 A | 5/1998 | Otten et al. |
| 5,755,693 A | 5/1998 | Walker et al. |
| 5,755,702 A | 5/1998 | Hillstead et al. |
| 5,766,203 A | 6/1998 | Imran et al. |
| 5,772,678 A | 6/1998 | Thomason et al. |
| 5,782,807 A | 7/1998 | Falvai et al. |
| 5,782,812 A | 7/1998 | Hart et al. |
| 5,782,817 A | 7/1998 | Franzel et al. |
| 5,800,414 A | 9/1998 | Cazal et al. |
| 5,807,350 A | 9/1998 | Diaz |
| 5,817,069 A | 10/1998 | Arnett |
| 5,843,031 A | 12/1998 | Hermann et al. |
| 5,853,393 A | 12/1998 | Bogert |
| 5,858,007 A | 1/1999 | Fagan et al. |
| 5,879,333 A | 3/1999 | Smith et al. |
| 5,885,217 A | 3/1999 | Gisselberg et al. |
| 5,895,376 A | 4/1999 | Schwartz et al. |
| 5,911,710 A | 6/1999 | Barry et al. |
| 5,916,194 A | 6/1999 | Jacobsen et al. |
| 5,919,160 A | 7/1999 | Sanfilippo, II |
| 5,921,968 A | 7/1999 | Lampropoulos et al. |
| 5,935,112 A | 8/1999 | Stevens et al. |
| 5,935,122 A | 8/1999 | Fourkas et al. |
| 5,944,695 A | 8/1999 | Johnson et al. |
| 5,951,518 A | 9/1999 | Licata et al. |
| 5,957,912 A | 9/1999 | Heitzmann |
| 5,967,490 A | 10/1999 | Pike |
| 5,971,958 A | 10/1999 | Zhang |
| 5,997,562 A | 12/1999 | Zadno-Azizi et al. |
| 6,017,352 A | 1/2000 | Nash et al. |
| 6,024,729 A | 2/2000 | Dehdashtian et al. |
| 6,027,480 A | 2/2000 | Davis et al. |
| 6,033,375 A | 3/2000 | Brumbach |
| 6,033,388 A | 3/2000 | Nordstrom et al. |
| 6,053,904 A | 4/2000 | Scribner et al. |
| 6,074,377 A | 6/2000 | Sanfilippo, II |
| 6,080,141 A | 6/2000 | Castro et al. |
| 6,083,207 A | 7/2000 | Heck |
| 6,086,570 A | 7/2000 | Aboul-Hosn et al. |
| 6,088,889 A | 7/2000 | Luther et al. |
| 6,106,540 A | 8/2000 | White et al. |
| 6,120,476 A | 9/2000 | Fung et al. |
| 6,120,480 A | 9/2000 | Zhang et al. |
| 6,120,494 A | 9/2000 | Jonkman |
| 6,142,981 A | 11/2000 | Heck et al. |
| 6,156,054 A | 12/2000 | Zadno-Azizi et al. |
| 6,159,198 A | 12/2000 | Gardeski et al. |
| 6,162,196 A | 12/2000 | Hart et al. |
| 6,171,281 B1 | 1/2001 | Zhang |
| 6,210,366 B1 | 4/2001 | Sanfilippo, II |
| 6,213,988 B1 | 4/2001 | McIvor et al. |
| 6,221,057 B1 | 4/2001 | Schwartz et al. |
| 6,228,062 B1 | 5/2001 | Howell et al. |
| 6,251,119 B1 | 6/2001 | Addis |
| 6,258,058 B1 | 7/2001 | Sanfilippo, II |
| 6,273,871 B1 | 8/2001 | Davis et al. |
| 6,276,661 B1 | 8/2001 | Laird |
| 6,277,108 B1 | 8/2001 | McBroom et al. |
| 6,287,280 B1 | 9/2001 | Lampropoulos et al. |
| D450,839 S | 11/2001 | Junker |
| 6,322,541 B2 | 11/2001 | West et al. |
| 6,331,176 B1 | 12/2001 | Becker et al. |
| 6,338,725 B1 | 1/2002 | Hermann et al. |
| 6,352,520 B1 | 3/2002 | Miyazaki et al. |

(56) References Cited

U.S. PATENT DOCUMENTS

| | | |
|---|---|---|
| 6,358,460 B1 | 3/2002 | Hunt, Jr. et al. |
| 6,361,559 B1 | 3/2002 | Houser et al. |
| 6,375,157 B1 | 4/2002 | Van de Lande |
| 6,402,723 B1 | 6/2002 | Lampropoulos et al. |
| 6,413,250 B1 | 7/2002 | Smith et al. |
| 6,416,499 B2 | 7/2002 | Paul, Jr. |
| 6,454,744 B1 | 9/2002 | Spohn et al. |
| 6,458,103 B1 | 10/2002 | Albert et al. |
| 6,494,860 B2 | 12/2002 | Rocamora et al. |
| 6,497,681 B1 | 12/2002 | Brenner |
| 6,508,790 B1 | 1/2003 | Lawrence |
| 6,520,939 B2 | 2/2003 | Lafontaine |
| 6,544,247 B1 | 4/2003 | Gardeski et al. |
| 6,551,283 B1 | 4/2003 | Guo et al. |
| 6,575,960 B2 | 6/2003 | Becker et al. |
| 6,589,214 B2 | 7/2003 | McGuckin, Jr. et al. |
| 6,589,262 B1 | 7/2003 | Honebrink et al. |
| 6,592,544 B1 | 7/2003 | Mooney et al. |
| 6,592,553 B2 | 7/2003 | Zhang et al. |
| 6,595,959 B1 | 7/2003 | Stratienko |
| 6,599,302 B2 | 7/2003 | Houser et al. |
| 6,623,460 B1 | 9/2003 | Heck |
| 6,632,200 B2 | 10/2003 | Guo et al. |
| 6,632,234 B2 | 10/2003 | Kieturakis et al. |
| 6,638,242 B2 | 10/2003 | Wilson et al. |
| 6,641,564 B1 | 11/2003 | Kraus |
| 6,645,178 B1 | 11/2003 | Junker et al. |
| 6,652,492 B1 | 11/2003 | Bell et al. |
| 6,655,660 B2 | 12/2003 | Wales |
| 6,663,595 B2 | 12/2003 | Spohn et al. |
| 6,666,853 B2 | 12/2003 | Chu et al. |
| 6,682,498 B2 | 1/2004 | Ross |
| 6,682,519 B1 | 1/2004 | Schon |
| 6,692,464 B2 | 2/2004 | Graf |
| 6,695,810 B2 | 2/2004 | Peacock, III et al. |
| 6,695,832 B2 | 2/2004 | Schon et al. |
| 6,712,789 B1 | 3/2004 | Lange et al. |
| 6,712,791 B2 | 3/2004 | Lui et al. |
| 6,719,749 B1 | 4/2004 | Schweikert et al. |
| 6,740,101 B2 | 5/2004 | Houser et al. |
| 6,776,774 B2 | 8/2004 | Tansey, Jr. et al. |
| 6,796,991 B2 | 9/2004 | Nardeo |
| 6,808,502 B2 | 10/2004 | Nguyen |
| 6,808,509 B1 | 10/2004 | Davey |
| 6,808,520 B1 | 10/2004 | Fourkas et al. |
| 6,814,718 B2 | 11/2004 | McGuckin, Jr. et al. |
| 6,827,709 B2 | 12/2004 | Fujii |
| 6,827,710 B1 | 12/2004 | Mooney et al. |
| 6,872,198 B1 | 3/2005 | Wilson et al. |
| 6,881,211 B2 | 4/2005 | Schweikert et al. |
| 6,887,220 B2 | 5/2005 | Hogendijk |
| 6,887,417 B1 | 5/2005 | Gawreluk et al. |
| 6,913,594 B2 | 7/2005 | Coleman et al. |
| 6,916,313 B2 | 7/2005 | Cunningham |
| 6,966,886 B2 | 11/2005 | Appling |
| 7,001,396 B2 | 2/2006 | Glazier et al. |
| 7,017,886 B1 | 3/2006 | Ngene-Igwe |
| 7,100,690 B2 | 9/2006 | Mullen et al. |
| 7,100,890 B2 | 9/2006 | Cote, Sr. et al. |
| 7,101,353 B2 | 9/2006 | Lui et al. |
| 7,166,088 B2 | 1/2007 | Heuser |
| 7,192,433 B2 | 3/2007 | Osypka et al. |
| 7,294,296 B2 | 11/2007 | Davey |
| 7,335,182 B1 | 2/2008 | Hilaire |
| 7,524,305 B2 | 4/2009 | Moyer |
| 7,637,893 B2 | 12/2009 | Christensen et al. |
| 8,105,315 B2 | 1/2012 | Johnson et al. |
| 8,403,890 B2 | 3/2013 | King et al. |
| 8,720,065 B2 | 5/2014 | Christensen et al. |
| 8,926,564 B2 | 1/2015 | King et al. |
| 8,932,260 B2 | 1/2015 | King et al. |
| 9,078,998 B2 | 7/2015 | King |
| 9,101,737 B2 | 8/2015 | King |
| 9,108,033 B2 | 8/2015 | Christensen et al. |
| 9,597,483 B2 | 3/2017 | King et al. |
| 2001/0001813 A1 | 5/2001 | West et al. |
| 2001/0041872 A1 | 11/2001 | Paul |
| 2001/0041873 A1 | 11/2001 | Dopper et al. |
| 2001/0041875 A1 | 11/2001 | Higuchi et al. |
| 2001/0049499 A1 | 12/2001 | Lui et al. |
| 2002/0010425 A1 | 1/2002 | Guo et al. |
| 2002/0038106 A1 | 3/2002 | Fujii |
| 2002/0042789 A1 | 4/2002 | Michalewicz et al. |
| 2002/0055715 A1 | 5/2002 | Young et al. |
| 2002/0068898 A1 | 6/2002 | McGuckin et al. |
| 2002/0068899 A1 | 6/2002 | McGuckin et al. |
| 2002/0072789 A1 | 6/2002 | Hackett et al. |
| 2002/0107482 A1 | 8/2002 | Rocamora et al. |
| 2002/0128604 A1 | 9/2002 | Nakajima |
| 2003/0014015 A1 | 1/2003 | Tansey et al. |
| 2003/0050604 A1 | 3/2003 | Lui et al. |
| 2003/0163139 A1 | 8/2003 | Graf |
| 2003/0216771 A1 | 11/2003 | Osypka et al. |
| 2004/0006330 A1 | 1/2004 | Fangrow |
| 2004/0030319 A1 | 2/2004 | Korkor et al. |
| 2004/0049499 A1 | 3/2004 | Nomoto et al. |
| 2004/0059296 A1 | 3/2004 | Godfrey |
| 2004/0065333 A1 | 4/2004 | Wilson et al. |
| 2004/0082913 A1 | 4/2004 | Spohn et al. |
| 2004/0092863 A1 | 5/2004 | Raulerson et al. |
| 2004/0092879 A1 | 5/2004 | Kraus et al. |
| 2004/0097863 A1 | 5/2004 | Appling |
| 2004/0097903 A1 | 5/2004 | Raulerson |
| 2004/0103229 A1 | 5/2004 | Callum |
| 2004/0122418 A1 | 6/2004 | Voorhees |
| 2004/0158208 A1 | 8/2004 | Hiejima |
| 2004/0167478 A1 | 8/2004 | Mooney et al. |
| 2004/0171997 A1 | 9/2004 | Wilson et al. |
| 2004/0172003 A1 | 9/2004 | Wilson et al. |
| 2004/0176739 A1 | 9/2004 | Stephens et al. |
| 2004/0176744 A1 | 9/2004 | Lange et al. |
| 2004/0176781 A1 | 9/2004 | Lindstrom et al. |
| 2004/0186444 A1 | 9/2004 | Daly et al. |
| 2004/0193112 A1 | 9/2004 | Glazier et al. |
| 2004/0193119 A1 | 9/2004 | Canaud et al. |
| 2004/0243095 A1 | 12/2004 | Nimkar et al. |
| 2004/0254534 A1 | 12/2004 | Bjorkman et al. |
| 2004/0254541 A1 | 12/2004 | Wong et al. |
| 2004/0260243 A1 | 12/2004 | Rickerd |
| 2004/0267202 A1* | 12/2004 | Potter ............ A61M 39/06 604/158 |
| 2005/0010238 A1 | 1/2005 | Potter et al. |
| 2005/0027257 A1 | 2/2005 | Davey |
| 2005/0049555 A1 | 3/2005 | Moorehead et al. |
| 2005/0049628 A1 | 3/2005 | Schweikert et al. |
| 2005/0090779 A1 | 4/2005 | Osypka |
| 2005/0113805 A1 | 5/2005 | Devellian et al. |
| 2005/0149060 A1 | 7/2005 | Thorstenson et al. |
| 2005/0245874 A1 | 11/2005 | Carrez et al. |
| 2005/0257838 A1 | 11/2005 | Enerson |
| 2005/0267487 A1 | 12/2005 | Christensen et al. |
| 2006/0030817 A1 | 2/2006 | Kraus et al. |
| 2006/0052749 A1 | 3/2006 | Moyer |
| 2006/0149293 A1 | 7/2006 | King et al. |
| 2007/0123825 A1 | 5/2007 | King et al. |
| 2007/0135794 A1 | 6/2007 | Raulerson et al. |
| 2008/0051717 A1 | 2/2008 | Voss et al. |
| 2008/0097386 A1 | 4/2008 | Osypka |
| 2008/0108976 A1 | 5/2008 | Johnson et al. |
| 2008/0300538 A1 | 12/2008 | Schweikert et al. |
| 2009/0105652 A1 | 4/2009 | Beal et al. |
| 2009/0131873 A1 | 5/2009 | Spear et al. |
| 2009/0143739 A1 | 6/2009 | Nardeo et al. |
| 2009/0177163 A1 | 7/2009 | King et al. |
| 2009/0218728 A1 | 9/2009 | Moyer |
| 2009/0234290 A1 | 9/2009 | Fisher et al. |
| 2009/0299291 A1 | 12/2009 | Baid |
| 2010/0094226 A1 | 4/2010 | Helgeson et al. |
| 2010/0101069 A1 | 4/2010 | Christensen et al. |
| 2012/0143138 A1 | 6/2012 | King et al. |
| 2012/0184913 A1 | 7/2012 | Christensen et al. |
| 2013/0226141 A1 | 8/2013 | King et al. |
| 2015/0119854 A1 | 4/2015 | King et al. |

(56) References Cited

U.S. PATENT DOCUMENTS

| | | |
|---|---|---|
| 2015/0290422 A1 | 10/2015 | King et al. |
| 2015/0290424 A1 | 10/2015 | King et al. |
| 2017/0182294 A1 | 6/2017 | King et al. |

FOREIGN PATENT DOCUMENTS

| | | |
|---|---|---|
| EP | 0442194 A2 | 8/1991 |
| EP | 1240916 A1 | 9/2002 |
| EP | 2651489 A1 | 10/2013 |
| IN | 2762/DELNP/2010 | 10/2011 |
| JP | 2007511089 T | 4/2007 |
| WO | 1998013083 | 4/1998 |
| WO | 2001049363 | 7/2001 |
| WO | 2004103229 A1 | 12/2004 |
| WO | 2005107843 A1 | 11/2005 |
| WO | 2007046850 A2 | 4/2007 |
| WO | 2007050788 A2 | 5/2007 |
| WO | 2007052278 A2 | 5/2007 |
| WO | 2009052327 A1 | 4/2009 |
| WO | 2009097274 A2 | 8/2009 |
| WO | 2009114456 A1 | 9/2009 |
| WO | 2010102240 A1 | 9/2010 |
| WO | 2012083245 A1 | 6/2012 |

OTHER PUBLICATIONS

U.S. Appl. No. 13/849,261, filed Mar. 22, 2013 Non-Final Office Action dated Aug. 5, 2014.
U.S. Appl. No. 13/849,261, filed Mar. 22, 2013 Notice of Allowance dated Feb. 27, 2015.
U.S. Appl. No. 14/585,592, filed Dec. 30, 2014 Notice of Allowance dated Mar. 16, 2015.
CN 200880121184.X filed Oct. 16, 2008 Decision of Rejection dated Dec. 4, 2012.
CN 200880121184.X filed Oct. 16, 2008 Office Action dated Aug. 20, 2012.
CN 200880121184.X filed Oct. 16, 2008 Office Action dated Feb. 16, 2012.
CN 201180060748.5 filed Jun. 17, 2013 First Office Action dated Oct. 28, 2014.
EP 08840257.3 Extended European Search Report dated Aug. 12, 2014.
EP 11848156.3 filed Jul. 16, 2013 extended European search report dated May 2, 2014.
Hazard Report—ECRI Problem Reporting System, Health Devices, May-Jun. 1996; vol. 25, No. 5-6, pp. 214-215.
PCT/US2005/015253 filed May 2, 2005 International Preliminary Report on Patentability dated Nov. 1, 2006.
PCT/US2005/015253 filed May 2, 2005 Search Report dated Aug. 4, 2005.
PCT/US2005/015253 filed May 2, 2005 Written Opinion dated Aug. 4, 2005.
PCT/US2008/080227 filed Oct. 16, 2008 International Preliminary Report on Patentability dated Apr. 20, 2010.
PCT/US2008/080227 filed Oct. 16, 2008 Search Report dated Dec. 23, 2008.
PCT/US2008/080227 filed Oct. 16, 2008 Written Opinion dated Dec. 23, 2008.
PCT/US2010/026409 filed Mar. 5, 2010 International Preliminary Report on Patentability dated Apr. 27, 2010.
PCT/US2010/026409 filed Mar. 5, 2010 Search Report dated Apr., 27, 2010.
PCT/US2010/026409 filed Mar. 5, 2010 Written Opinion dated Apr. 27, 2010.
PCT/US2011/065632 filed Dec. 16, 2011 International Preliminary Report on Patentability dated Jun. 18, 2013.
PCT/US2011/065632 filed Dec. 16, 2011 International Search Report dated Apr. 4, 2012.
PCT/US2011/065632 filed Dec. 16, 2011 Written Opinion dated Apr. 4, 2012.
U.S. Appl. No. 11/288,959, filed Nov. 29, 2005 Advisory Action dated Feb. 28, 2014.
U.S. Appl. No. 11/288,959, filed Nov. 29, 2005 Final Office Action dated Dec. 6, 2013.
U.S. Appl. No. 11/288,959, filed Nov. 29, 2005 Final Office Action dated Jun. 22, 2009.
U.S. Appl. No. 11/288,959, filed Nov. 29, 2005 Non-Final Office Action dated Mar. 29, 2013.
U.S. Appl. No. 11/288,959, filed Nov. 29, 2005 Non-Final Office Action dated Oct. 20, 2008.
U.S. Appl. No. 11/531,339, filed Sep. 13, 2006 Advisory Action dated Mar. 14, 2014.
U.S. Appl. No. 11/531,339, filed Sep. 13, 2006 Advisory Action dated Nov. 30, 2012.
U.S. Appl. No. 11/531,339, filed Sep. 13, 2006 Final Office Action dated Dec. 6, 2013.
U.S. Appl. No. 11/531,339, filed Sep. 13, 2006 Final Office Action dated Sep. 24, 2012.
U.S. Appl. No. 11/531,339, filed Sep. 13, 2006 Non-Final Office Action dated Apr. 2, 2013.
U.S. Appl. No. 11/531,339, filed Sep. 13, 2006 Non-Final Office Action dated Dec. 27, 2011.
U.S. Appl. No. 11/531,339, filed Sep. 13, 2006 Non-Final Office Action dated Jun. 19, 2014.
U.S. Appl. No. 11/531,339, filed Sep. 13, 2006 Notice of Allowance dated Sep. 11, 2014.
U.S. Appl. No. 12/252,975, filed Oct. 16, 2008 Final Office Action dated Jan. 19, 2011.
U.S. Appl. No. 12/252,975, filed Oct. 16, 2008 Final Office Action dated Nov. 8, 2012.
U.S. Appl. No. 12/252,975, filed Oct. 16, 2008 Non-Final Office Action dated Apr. 11, 2012.
U.S. Appl. No. 12/252,975, filed Oct. 16, 2008 Non-Final Office Action dated Sep. 8, 2010.
U.S. Appl. No. 12/252,975, filed Oct. 16, 2008 Notice of Allowance dated Aug. 20, 2013.
U.S. Appl. No. 12/252,975, filed Oct. 16, 2008 Notice of Panel Decision dated Dec. 9, 2011.
U.S. Appl. No. 12/399,749, filed Mar. 6, 2009 Final Office Action dated Oct. 11, 2012.
U.S. Appl. No. 12/399,749, filed Mar. 6, 2009 Non-Final Office Action dated Mar. 28, 2012.
U.S. Appl. No. 12/648,533, filed Dec. 29, 2009 Decision on Appeal dated Feb. 2, 2015.
U.S. Appl. No. 12/648,533, filed Dec. 29, 2009 Examiner's Answer dated Dec. 22, 2011.
U.S. Appl. No. 12/648,533, filed Dec. 29, 2009 Final Office Action dated Jan. 19, 2011.
U.S. Appl. No. 12/648,533, filed Dec. 29, 2009 Non-Final Office Action dated Sep. 13, 2010.
U.S. Appl. No. 12/648,533, filed Dec. 29, 2009 Notice of Panel Decision dated Jun. 16, 2011.
U.S. Appl. No. 13/329,141, filed Dec. 16, 2011 Advisory Action dated Jul. 11, 2014.
U.S. Appl. No. 13/329,141, filed Dec. 16, 2011 Final Office Action dated May 8, 2014.
U.S. Appl. No. 13/329,141, filed Dec. 16, 2011 Non-Final Office Action dated Feb. 14, 2014.
U.S. Appl. No. 13/434,415, filed Mar. 29, 2012 Non-Final Office Action dated Aug. 15, 2013.
U.S. Appl. No. 13/434,415, filed Mar. 29, 2012 Notice of Allowance dated Dec. 26, 2013.
CN 201180060748.5 filed Jun. 17, 2013 Second Office Action dated Jun. 17, 2015.
EP 11848156.3 filed Jul. 16, 2013 Examination Report dated Nov. 3, 2015.
U.S. Appl. No. 14/749,323, filed Jun. 24, 2015 Notice of Allowance dated Nov. 9, 2015.
U.S. Appl. No. 14/749,418, filed Jun. 24, 2015 Notice of Allowance dated Oct. 23, 2015.
CN 201180060748.5 filed Jun. 17, 2013 Decision of Re-examination dated Sep. 21, 2016.

(56) References Cited

OTHER PUBLICATIONS

CN 201180060748.5 filed Jun. 17, 2013 Notice of Re-examination dated Jun. 15, 2016.
CN 201180060748.5 filed Jun. 17, 2013 Third Office Action dated Dec. 23, 2015.
U.S. Appl. No. 11/288,959, filed Nov. 29, 2005 Non-Final Office Action dated Jul. 14, 2016.
U.S. Appl. No. 11/288,959, filed Nov. 29, 2005 Notice of Allowance dated Nov. 4, 2016.

* cited by examiner

VALVED SHEATH INTRODUCER FOR VENOUS CANNULATION

CROSS-REFERENCE TO RELATED APPLICATIONS

This application is a division of U.S. patent application Ser. No. 12/648,533, filed Dec. 29, 2009, now U.S. Pat. No. 9,108,033, which is a division of U.S. patent application Ser. No. 11/119,599, filed May 2, 2005, now U.S. Pat. No. 7,637,893, which claims the benefit of U.S. Provisional Application No. 60/566,896, filed Apr. 30, 2004, each of which is expressly incorporated by reference as if fully set forth herein.

BACKGROUND OF THE INVENTION

Introducer devices are commonly utilized for inserting medical devices, such as venous access catheters, into patients. Typically, such introducer devices comprise a peel-away sheath and a hub/handle assembly which is used in conjunction with a dilator assembly to access the vein of a patient, following insertion of a needle and guidewire. In particular, procedures for introducing a catheter into a blood vessel include the cut-down method and the Seldinger technique. The Seldinger technique involves first inserting a needle through the skin of a patient and into a vein to be catheterized, inserting a guidewire through the needle and into the vein, removing the needle from the guidewire and inserting the dilator and introducer sheath over the guidewire and into the vein, simultaneously removing the dilator and guidewire from the introducer sheath, inserting a catheter through the introducer sheath and into position within the accessed vein. Following insertion of the catheter, the introducer sheaths are generally designed such that they can be peeled away from the catheter, without affecting the catheter positioning within the vein. Such introducer sheaths and assemblies are described, for example, in U.S. Pat. No. 4,772,266 to Groshong, issued Sep. 20, 1988, and U.S. Pat. No. 4,306,562 to Osborne, issued Dec. 21, 1981, each of which is incorporated by reference herein.

Problems, however, with the above-described procedure include, 1) that upon removal of the dilator and guidewire from the sheath, blood loss through the sheath can occur, and 2) that the introducer sheath provides a conduit for the introduction of air into the patient's vein, which can result in air embolism. Moreover, the risk of air embolism increases in proportion to the diameter size of the indwelling sheath, meaning that larger diameter sheaths routinely used for the placement of larger diameter catheters would increase such risk. Thus, there have been a variety of solutions proposed, which involve the incorporation of a valve in the proximal end of the introducer sheath, which would allow passage of a guidewire and dilator while simultaneously preventing blood loss or the introduction of air through the sheath. Such proposed solutions can be found, for example, in U.S. Pat. No. 5,125,904 to Lee, issued Jun. 30, 1992, U.S. Pat. No. 5,397,311 to Walker et al., issued Mar. 14, 1995, U.S. Pat. No. 6,083,207 to Heck, issued Jul. 4, 2000, each of which is incorporated by reference herein.

The aforementioned and similarly directed patents are concerned primarily with providing an elastic valve structure that provides hemostasis and the prevention of blood loss or bleed back for arterial cannulation procedures where there is significant positive blood pressure. On the other hand, with respect to venous cannulation, blood pressure is much lower and negative pressures may be involved, meaning that while prevention of blood loss is an ancillary concern, it is the prevention of air embolism that is the most crucial consideration. Thus, there exists the need for a valved sheath introducer designed for particular use for venous cannulation.

BRIEF SUMMARY OF THE INVENTION

Accordingly, the present invention is directed to a valved sheath introducer for venous cannulation. In one embodiment of the invention, the valve in the introducer includes a thin disk with a central slit and includes features such as opposing anchors to allow stretching of the disk when a medical device is inserted therethrough, a thickened central portion through which a self-sealing slit is positioned, which promotes optimal resealing upon removal of a medical device, and mechanical or other means of splitting the disk simultaneous to the breaking and separating of a sheath handle from an inserted medical device. In one embodiment, the thickened central portion or island has a concave surface. Some embodiments of the valve include slits or notches aligned with the central slit to facilitate separation of the valve when the sheath and handle are removed from an inserted medical device.

In another embodiment of the invention, an apparatus for insertion of a medical device into a body comprises a sheath comprising a sheath body and a handle, the handle including at least one receiving section, a valve comprising a slit through a central portion thereof and at least one anchoring member configured for insertion into the handle receiving section, the anchoring member being positioned along an edge of the valve, and a cap attached to the handle, at least a portion of the valve being compressed therebetween. In another embodiment, a wire is looped through a slit positioned in the valve, such that when the handle is separated and removed from medical device inserted through the valved sheath introducer, the wire cuts the valve into two portions.

In one aspect of the valved sheath introducer, the valve is designed to provide optimal sealing when removing an instrument, such as a dilator. The optimal sealing occurs due to the configuration of the valve, such as a central portion or island and one or more anchoring members, and the way in which the valve is tightly held between a handle and a cap. Thus, upon removal of an instrument from the introducer sheath, the valve body, which is stretched as the instrument is inserted therethrough, rebounds toward the handle but cannot resume its original position due to the pressure exerted by the cap and the handle. The result is a bunching or duckbill effect of the valve that provides a desirable seal.

These and other embodiments, features and advantages of the present invention will become more apparent to those skilled in the art when taken with reference to the following more detailed description of the invention in conjunction with the accompanying drawings that are first briefly described.

DETAILED DESCRIPTION OF THE INVENTION

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

The present invention involves valves and valved sheath introducers used particularly in venous cannulation procedures. However, it should be appreciated that while the designs described herein are intended for such use, they may be equally suitable for a variety of other uses (e.g., arterial cannulation, introduction of pacing leads, etc.) and therefore should not be so limited. Further, while sheath introducers and sheath introducer assemblies are described herein for exemplary purposes of housing and implementation of the subject valves, it should be appreciated that many different configurations and types of sheath introducers and sheath introducer assemblies would be equally suitable for use with the valves of the present invention and therefore should in no way serve to limit the scope of the valves described herein. In addition, as used in this specification and the appended claims, the singular forms "a," "an" and "the" include plural referents unless the context clearly dictates otherwise. Thus, for example, the term "a slit" is intended to mean a single slit or more than one slit.

Figure 1:
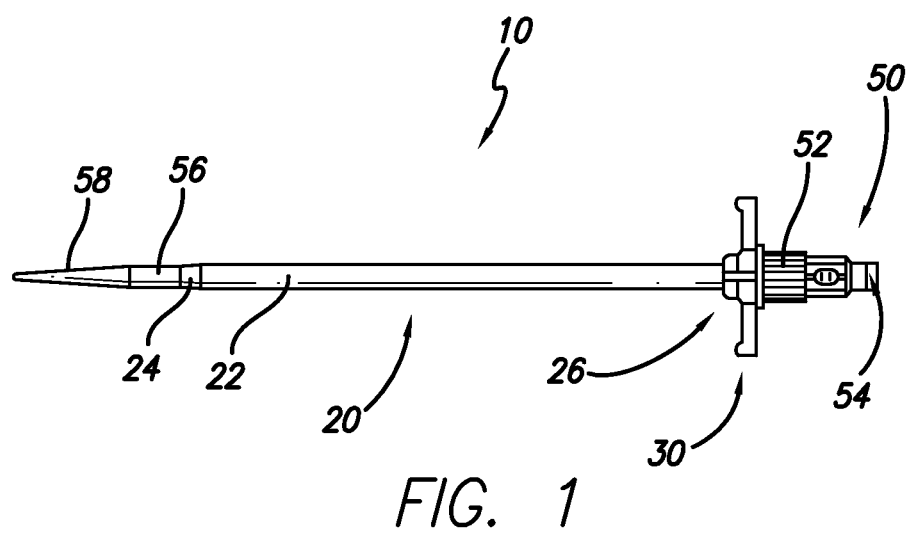
FIG. 1 illustrates a side perspective view of one embodiment of a valved sheath introducer with an inserted dilator.
Figure 2:
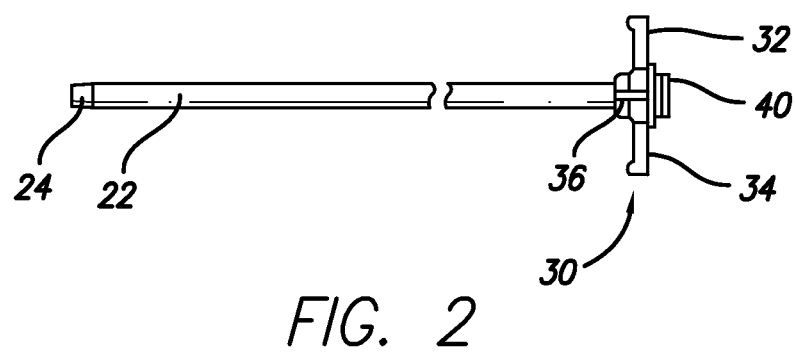
FIG. 2 illustrates a side perspective view of the sheath introducer of FIG. 1 in isolation.
Figure 4:
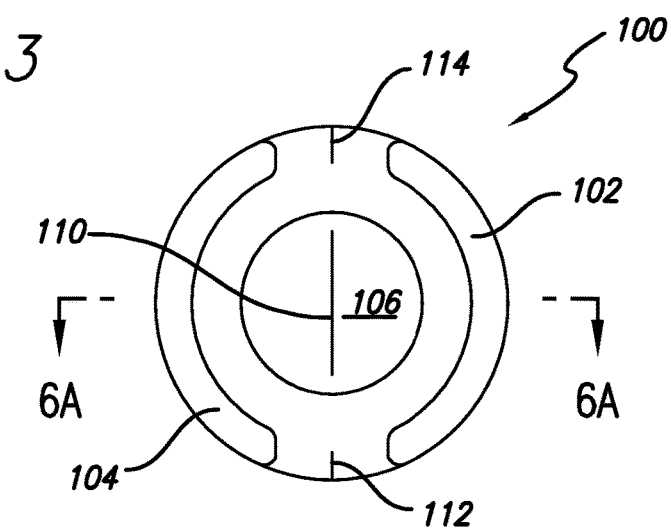
FIG. 4 illustrates a bottom view of one embodiment of a valve for a valved sheath introducer.

Referring now to FIGS. 1 and 2, a valved sheath introducer assembly 10 according to one embodiment is shown, including a valved sheath introducer 20 and a dilator 50. The valved sheath introducer assembly 10 is shown in its insertion configuration with dilator 50 inserted completely through the valved sheath introducer 20 and locked thereto. The valved sheath introducer 20 includes a sheath body 22, a handle 30, a cap 40, and an internal valve 100 (FIG. 4). In this embodiment, the handle 30 has a first side 32 and a second side 34 separated by two slots 36, positioned approximately 180° apart. The sheath body 22 has a tapered distal end 24 to facilitate insertion into a blood vessel. In one embodiment, the sheath body 22 is made of polytetrafluoroethylene (PTFE) and the handle 30 and cap 40 are made of K-Resin® (styrene-butadiene copolymer). In another embodiment, the handle 30 and cap 40 are made of Cryolite® (poly(methyl methacrylate)). Of course, other materials are also possible for the sheath body, handle and cap, including other polymer materials (e.g., polycarbonate, thermoplastics, etc.), as is apparent to one of ordinary skill in the art.

Figure 3:
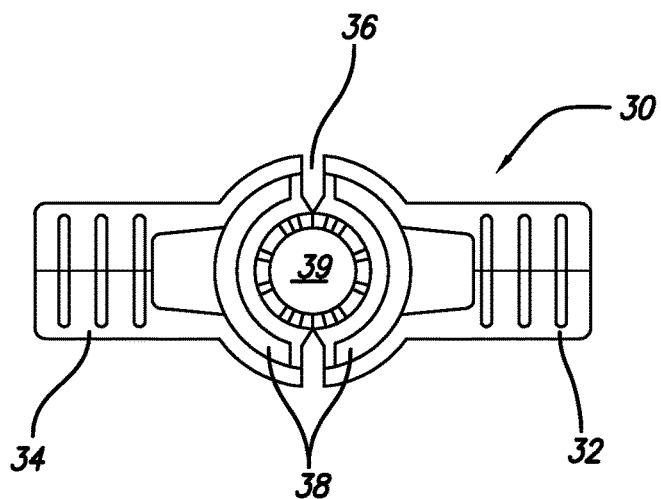
FIG. 3 illustrates a top view of the handle of the sheath introducer of FIG. 2.

In an exemplary manufacturing process for the valved sheath introducer 20, the handle 30 is insert molded over the proximal end 26 of the sheath body 22. After molding, the valve 100 is placed on the top of the handle 30, and the cap 40 is attached to the handle 30 (e.g., via ultrasonic weld, adhesives, screws, etc.) over the valve 100 under force. In one exemplary manufacturing method, the attachment method is ultrasonic welding wherein the sheath body 22 and handle 30 are placed into an ultrasonic welder and the cap 40 is pressed onto the handle 30 after the valve 100 has been set therein. The ultrasonic welder sends vibrations through the cap 40, causing a portion of the cap 40 and handle 30 to meld together. In one embodiment, the cap 40 is in two part form prior to welding such that a small gap in alignment with the slots 36 can be provided. In a top view of the handle 30, shown in FIG. 3 prior to attachment of the valve 100 and cap 40, slots 36 can be seen in more detail as can the handle bore 39, which is configured to be approximately the same diameter as that of the lumen of the valved sheath introducer 20. In addition, valve receiving sections 38 can be seen configured to accommodate valve anchors 102, 104 (FIG. 4), as will be explained in more detail below.

Referring back to FIG. 1, the dilator 50 includes a threaded luer connector 52, which rotates independently of the dilator body 56, and is configured for mating with the cap 40 to lock the dilator 50 to the valved sheath introducer 20. The body 56 has a diameter approximately equal to that of the lumen of the valved sheath introducer 20 and also has a tapered distal end 58 to provide ease of insertion of the valved sheath introducer assembly 10 into a blood vessel. The dilator 50 also includes a luer connection 54 at the proximal end thereof for attachment to devices used for purposes such as flushing. An injection cap (not shown) may also be placed over the proximal end of the dilator.

Figure 5:
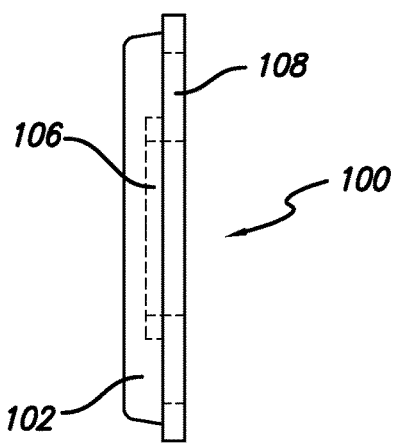
FIG. 5 illustrates a side view of the valve of FIG. 4.

FIGS. 4-6B illustrate one embodiment of a valve 100 for incorporation into a valved sheath introducer. FIG. 4 is a bottom view of valve 100, which is a thin disk-like body 108, including valve anchors 102, 104 around the circumferential edge of the body 108 and disposed on the back side thereof. The valve anchors 102, 104 extend from the body 108, as can be seen in FIGS. 5 and 6A, and are configured in size and shape to correspond with the valve receiving sections 38 of the handle 30 (FIG. 3) to ensure that the valve 100 remains in axial position as instruments are inserted therethrough and withdrawn therefrom, and also to ensure that the valve 100 properly separates (each side of the valve remaining with its respective side of the handle into which it is held) upon removal of the sheath introducer 20 from an inserted instrument.

Figure 6A:
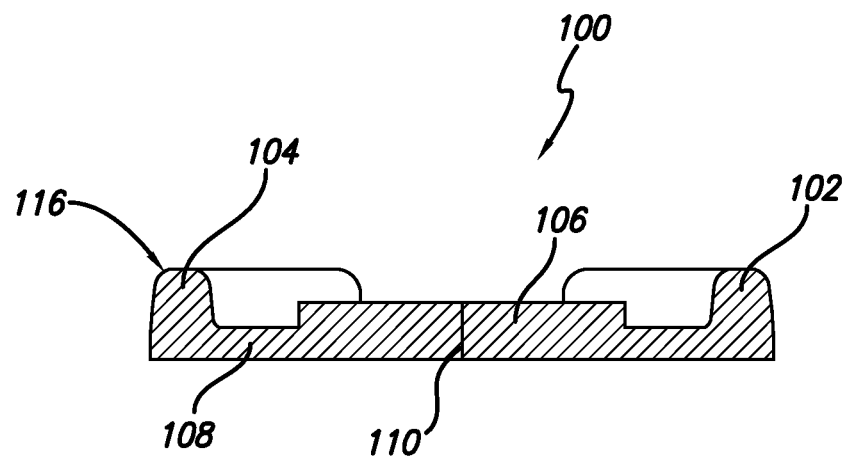
FIGS. 6A and 6B illustrate a cross-sectional view of the valve of FIG. 4.
Figure 6B:
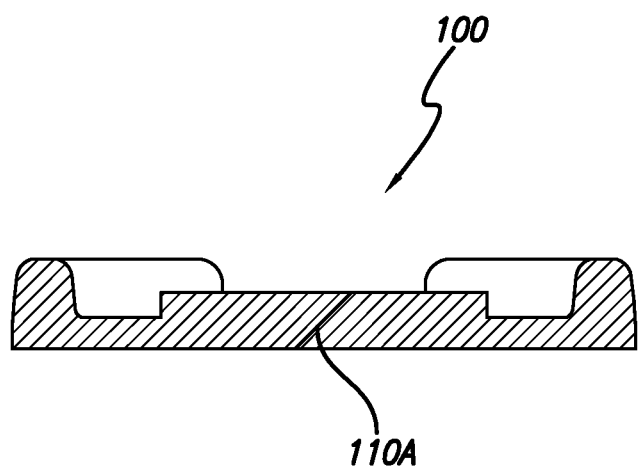

FIG. 6A is a cross-section of the valve of FIG. 4 taken along line 6A-6A, showing the relative thickness of the island 106 compared to the opposing anchors 102, 104. As shown in this embodiment, the island thickness is slightly less than that of the anchors, although in other embodiments, the island thickness is either the same or greater than the thickness of the anchors. In still other embodiments, the anchors 102, 104 have different thicknesses, each of which may be greater than, less than or equal to the island thickness. Also, in the embodiments shown, the anchors 102, 104 have rounded edges 116, although other configurations, including edges with opposing right angles, are certainly contemplated herein. FIG. 6B illustrates another embodiment of the valve 100, including a slit 110A that is cut through the middle region of the valve 100, traversing at an angle from a top surface of the valve to a bottom surface thereof (e.g., to a surface of the island 106) that is different from the approximately 90° angle with respect to the top surface of the valve shown in FIG. 6A. While the slit 110A is shown as cut at approximately a 45° angle, certainly any other non-parallel angle with respect to the top surface of the valve is possible as should be appreciated by one of ordinary skill in the art.

The anchors 102, 104 allow for a tight tolerance with respect to the positioning of the valve 100 within the handle 30, being tightly secured therein by the cap 40, as explained above. This tight tolerance results in an advantageous reaction by the valve 100 with respect to sealing thereof upon removal of an instrument that had previously been inserted therethrough (e.g., dilator, etc.). In particular, in concert with the island 106, which is a circular feature positioned in the center of the body 108, extending along with the anchors 102, 104 from the bottom thereof, a superior seal is created upon removal of an instrument from the sheath introducer 20, as will be explained below in connection with FIGS. 9A-9D. It should be appreciated that while the valve 100 has a circular shape and the valve anchors 102, 104 have a semi-circular shape, as seen in FIG. 4, various shapes and sizes are possible and contemplated herein to correspond with the shape and size of the handle and receiving sections onto/into which they are positioned.

Figure 7:
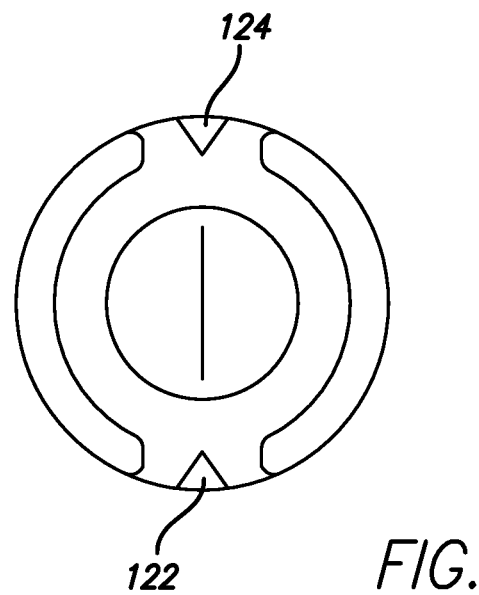
FIG. 7 illustrates a bottom view of another embodiment of a valve for a valved sheath introducer.
Figure 8:
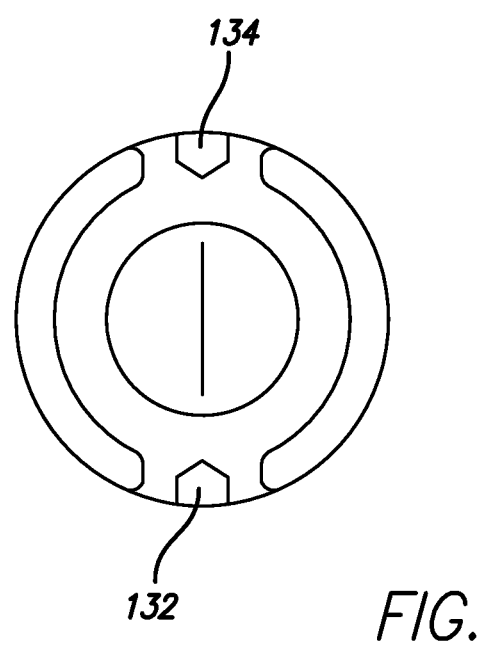
FIG. 8 illustrates a bottom view of yet another embodiment of a valve for a valved sheath introducer.

In the embodiment shown in FIG. 4, approximately equidistantly spaced on the edge of the body 108 between the valve anchors 102, 104 on opposite sides of the body 108 are peripheral slits 112, 114, which enable the valve 100 to be easily split in half along the line extending from slit 112 to slit 114. These slits can also be in the form of notches having various shapes, two of which (122, 124 and 132, 134) are illustrated in FIGS. 7 and 8. While the notches shown are in the shapes of triangles and trapezoids, other shapes are possible and are contemplated herein to facilitate the separation of the valve 100. A central slit 110 through which instruments can be inserted is cut through the valve body 108 and island 106 and is positioned approximately centrally with respect to the edges of the valve 100. While only one slit is shown, in other embodiments two or more slits are formed through the valve in different patterns. For instance, in one embodiment, multiple slits are cut through the valve in a pattern similar to an asterisk when viewed from the top or bottom thereof. As discussed, when the valve 100 is placed into the handle 30, the valve anchors 102, 104 are positioned in receiving sections 38 of the handle 30, which places the island 106 within the opening of the handle bore 39. Such alignment results in the slits 112, 114 being aligned with the slots 36 of the handle 30.

The following materials and dimensions are provided as an example of one embodiment and should not be taken as limiting the invention in any way. The valve 100 in this embodiment is made of silicone (Dow Corning Q7-4840), having a diameter of approximately 0.516 inches, while the diameter of the island 106 is approximately 0.260 inches and the distance between inner edges of the islands 102, 104 is approximately 0.420 inches (the width of the anchors thus being approximately 0.048 inches). The thickness of the valve 100 along the anchors 102, 104 is approximately 0.090 inches, while the thickness of the valve across the island is approximately 0.045 inches, the remainder of the body therefore having a thickness of approximately 0.025 inches. The distance between the anchors 102, 104 is approximately 0.160 inches on both sides of the valve 100. The central slit 110 has a length of approximately 0.204 inches, while the peripheral slits 112, 114 have a length of approximately 0.050 inches. In other embodiments, the dimensions are dependent upon the size of the instrument(s) being inserted through the valve.

Figure 14:
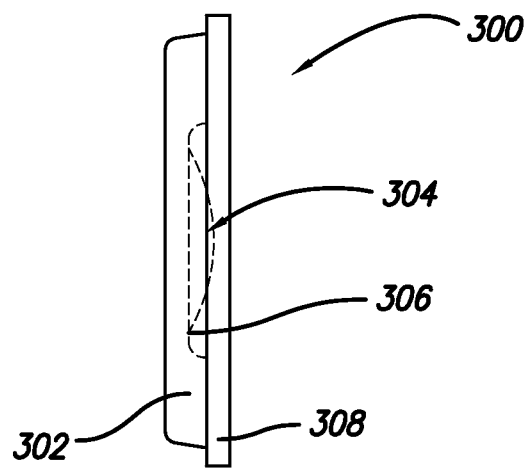
FIG. 14 is an alternate embodiment of a valve with an island, the island having a concave surface.
Figure 15:
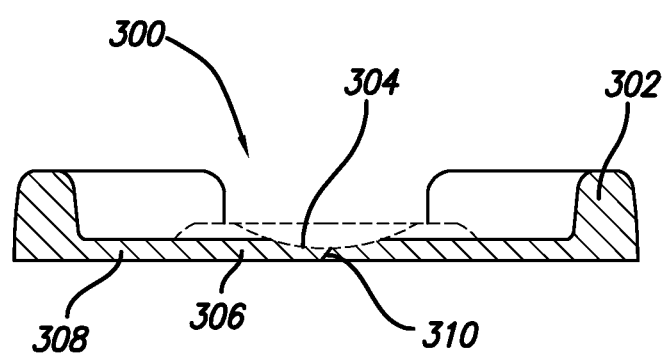
FIG. 15 is a cross-sectional view of the valve of FIG. 14.

With respect to the valve island 106, another embodiment is shown in FIGS. 14 and 15. Valve 300 is shown, including one or more anchors 302 and an island 306 that has a concave surface 304 extending into the thickness of the valve body 308 and a slit 310. The slit 310 as shown is positioned at an angle of approximately 60° with respect to the top surface of the valve, although as stated above in connection with FIGS. 6A and 6B, any other non-parallel angle with respect to the top surface of the valve is possible. The curvature of the concave surface can be more or less than shown and can extend short of, or up to, the line of the valve body in other embodiments. The depth of the concavity is also variable, which alters the thickness of the midpoint of the island in different embodiments. As shown in FIG. 15, the edges of the island are curved, although as with the anchors, other types of edges are possible. Numerous embodiments are contemplated with respect to the configuration of the island and slits or notches in the valve. For instance, the valve could have a concave surface on the island along with notches on opposing sides of the valve, the valve could have a concave surface on the island and an opposing concave surface on the top of the valve with no slits or notches, the valve could have notches or slits but no island, etc.

Figure 9A:
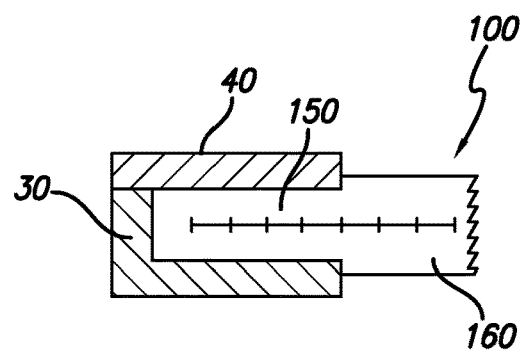
FIGS. 9A-9D illustrates an advantageous feature of one embodiment of a valve for a valved sheath introducer.
Figure 9B:
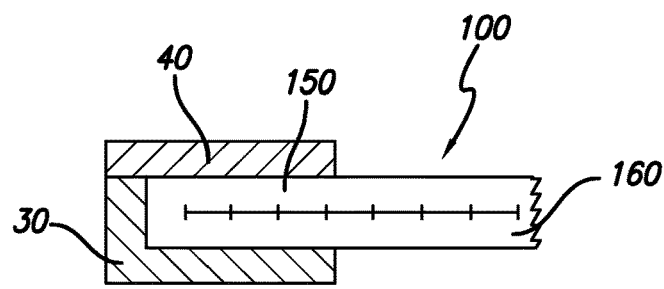
Figure 9C:
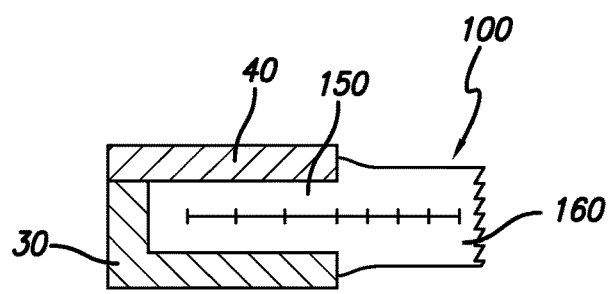

FIGS. 9A-9C depict the configuration of one side of the valve 100 with respect to the handle 30 and the cap 40 as an instrument is inserted therethrough (FIG. 9B) and withdrawn therefrom (FIG. 9C). An imaginary grid is provided to aid in the illustration of the movement and positioning of the valve 100 with respect to the handle 30 and the cap 40. It should be appreciated, however, that the grid is exemplary only and isn't intended to depict actual distances or precise intervals. In FIG. 9A, the valve 100 is tightly held between the handle and the cap prior to insertion of an instrument therethrough. Close inspection of the valve 100 reveals that the thickness of the valve material 150 between the handle 30 and the cap 40 is slightly less than the thickness of the valve material 160 outside of this area (i.e., within the handle bore 39). This is due to the pressure exerted onto the valve 100 as the cap 40 is attached to the handle 30 as explained above. As can be seen, the distance between the marks on the grid line in FIG. 9A are the same for both valve material 150 and 160.

FIG. 9B depicts the movement of the valve 100 upon insertion of an instrument therethrough, the valve material 160 stretching and experiencing a reduction in thickness such that the thickness thereof is approximately equivalent to the thickness of valve material 150 (although certainly the thickness of the valve material 160 could be greater than or equal to the valve material 150 as it is stretched upon insertion of an instrument through valve 100). In addition to the thickness of the valve, this demonstration of stretching is evidenced by the increased distance between the marks on the grid line along valve material 160. Although the valve material 150 is still held tightly between the cap 40 and the handle 30 while an instrument is inserted through the valve 100, stretching of the material does occur. This action is revealed in FIG. 9B by the grid line as the distance between the marks on the grid line is shown to increase. It is noted here that while the material adjacent to the anchors stretches slightly upon insertion of an instrument through the valve 100, the anchors themselves remain in position inside the receiving sections of the handle.

Figure 9D:
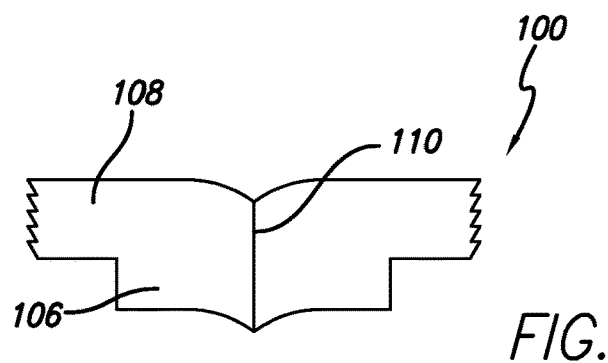

FIG. 9C depicts the valve 100 upon removal of the inserted instrument, at which point the valve material 150 and 160 rebounds back toward the side of the handle 30. However, because the valve material 150 is tightly held between the cap 40 and the handle 30, a bunching effect occurs as stretched valve material 150 that has moved from an original position between the handle 30 and cap 40 toward the center of the valved introducer 20 is prevented from returning to its original position. This phenomenon is illustrated by the grid line in FIG. 9C, which shows the distance between marks in valve material 150 to be approximately the same as the distance in FIG. 9B, whereas the distance between marks in valve material 160 has slightly decreased. This bunching effect leads to a duckbill-like configuration for the valve 100 as shown in FIG. 9D, which illustrates the configuration of the central region of the valve following removal of an instrument. Such a configuration provides a superior seal over the valves of the prior art. In one embodiment, the valve 100 is provided with a lubricant in order to ease the surface friction between the valve and inserted instrument, thus maintaining the desired duckbill shape.

Removal of the sheath introducer 20 from an instrument inserted therethrough (e.g., a catheter) is effectuated by grasping the handle 30 on each side thereof and pulling the sides in opposite directions so that the handle 30 cracks along the slots 36. Upon cracking and splitting of the handle 30, the integrated valve 100 tears along the slit line created by central slit 110 and peripheral slits 112, 114, the tearing process enabled, as discussed above, by the anchors 102, 104, which maintain the position of each side of the valve 100 within the respective side of the handle. As the two pieces of the handle are pulled away from one another, the sheath peels down its entire length at the circumferential location of the handle slots (which correspond to the aligned pre-split sections of the sheath). Due to the extrusion process for manufacturing the PTFE, which results in an alignment of the molecules, the peeling of the sheath is continuous down the entire length thereof at the circumferential locations without the need for score line(s). The handle does not detach from the sheath during or after the splitting process. In other embodiments of the invention, the sheath is made from PTFE or another like polymer material with one or more score lines positioned longitudinally along the length of the sheath in line with the slot(s) in the handle.

Figure 10:
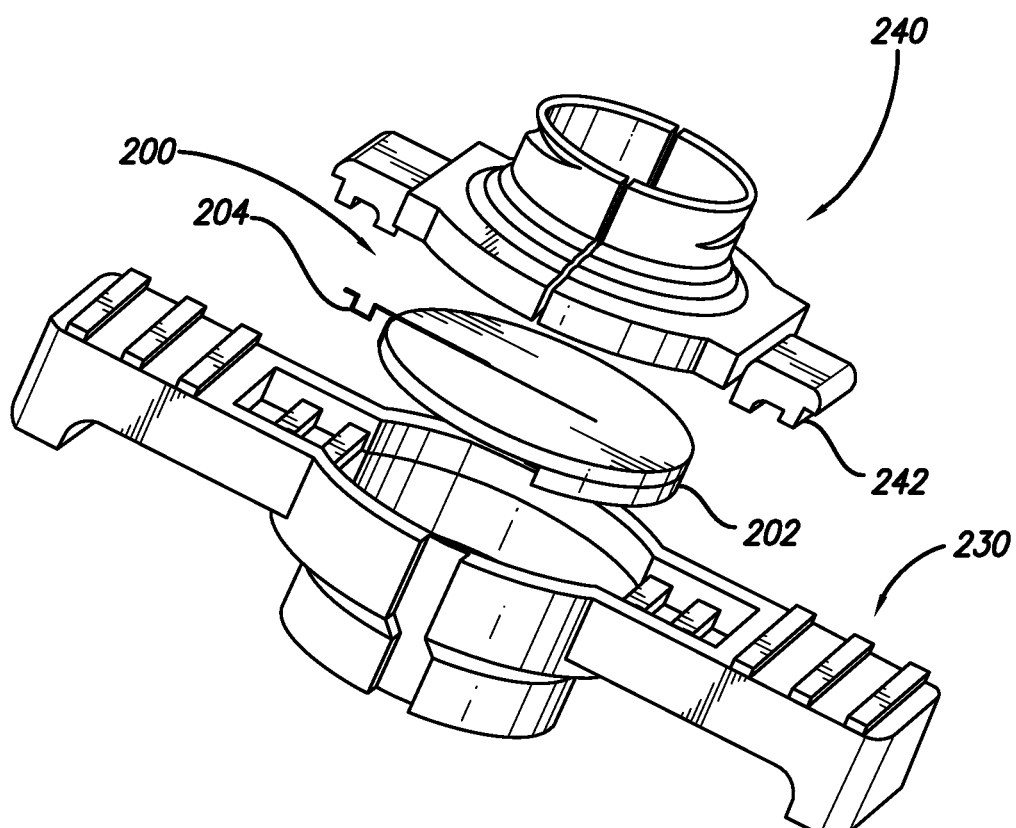
FIG. 10 depicts an alternate embodiment of a valve for a valved sheath introducer along with a handle and cap prior to assembly.
Figure 11:
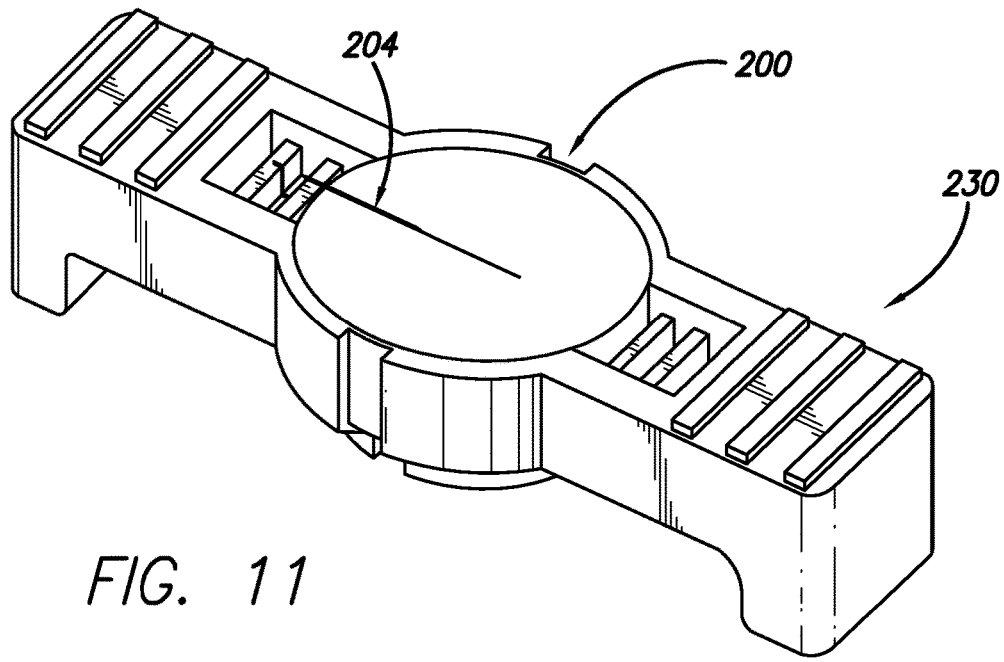
FIG. 11 depicts the valve of FIG. 10 in isolation with the handle.
Figure 12:
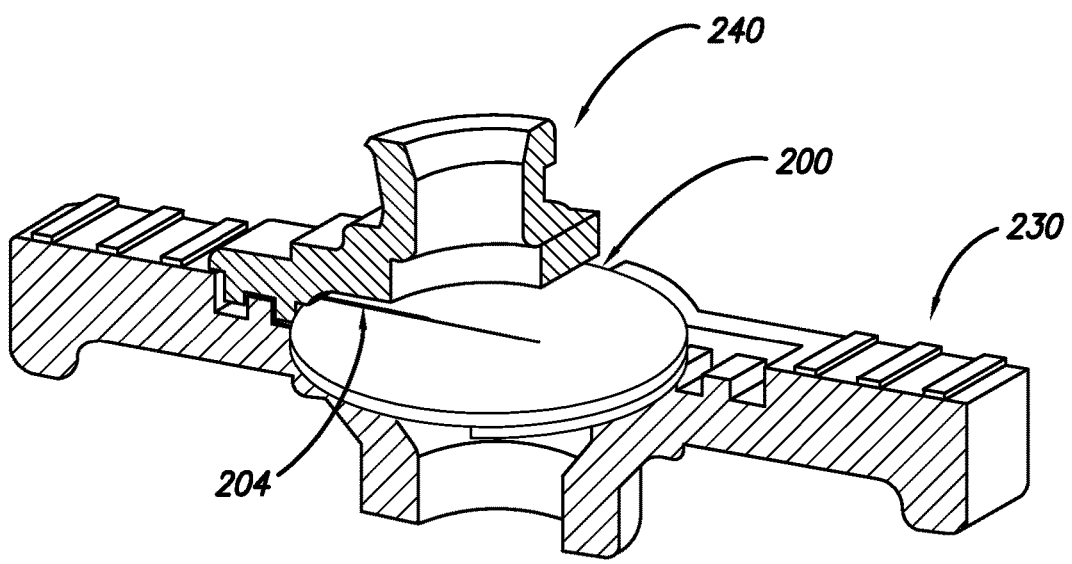
FIG. 12 is a cross-sectional assembled view of the cap, handle and valve of FIG. 10.
Figure 13:
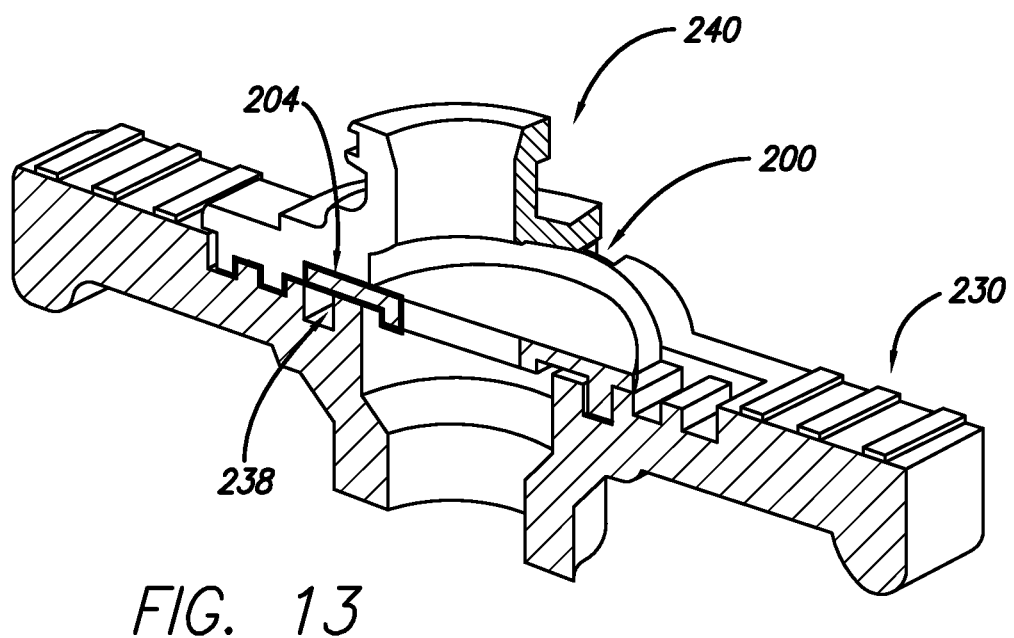
FIG. 13 is a further cross-sectional view of the cap, handle and valve of FIG. 12.

In another embodiment of a valved sheath introducer, a very thin wire is associated with the valve, as shown in FIGS. 10-13. FIG. 10 illustrates a handle 230, a cap 240 and a valve 200, which includes a single anchor 202 and a thin wire 204, prior to assembly. The wire 204 is looped through the central slit of the valve 200 and each end extends beyond the edge of the valve 200, being coupled together for positioning in the handle 230. The central slit of valve 200 is oriented perpendicular to the slots of the handle 230, differently than the axial alignment of valve 100 described above. It should be noted that in this view, the cap 240 has an extension pattern 242 configured to be received within a like shaped extension pattern in the handle 230 for an improved connection therebetween. FIG. 11 illustrates the valve 200 placed into the handle 30. FIG. 12 illustrates the interaction of the handle 230, cap 240 and valve 200 by showing a cutaway view of the cap 240 and handle 230 with a top perspective view of the valve, while FIG. 13 shows another cutaway view of the handle 230 and cap 240 with a cross-sectional view of the valve 200 also being shown.

In FIG. 13, the side of the handle 230 that receives the wire 204 can be seen to also have an empty receiving section 238 due to the fact that the valve 200 does not contain an anchor for positioning therein. While in some embodiments, this empty section does not exist, in this particular embodiment the presence of receiving sections in both sides of the handle 230 facilitates manufacture of the valved sheath introducer by permitting positioning of the anchor 202 in either side of the handle. When the handle 230 is broken to remove from an inserted instrument (e.g., a catheter), the wire 204 remains with the half of the handle 230 into which the extension thereof has been set (FIG. 11), while the valve 200 remains with the opposite half, into which the anchor 202 is set (FIGS. 12, 13). Thus, as the halves of the handle 230 are pulled in opposite directions, the wire 202 cuts the valve 200, slicing it into two parts for easy removal from the inserted instrument.

The valved sheath introducer described herein is used according to one embodiment as follows. After an access site on a body is determined and an incision made, the valved sheath introducer assembly is inserted into the body with a distal end of the sheath body extending into a body vessel to be accessed. Following optional preparatory steps (e.g., flushing), the dilator is removed from the valved sheath introducer. As the dilator is removed, the valve closes as described above in connection with FIGS. 9A-9C. A catheter or other medical device can then be inserted through the valved sheath introducer and into the body vessel. When the desired positioning of a more permanent medical device, such as a catheter, has been accomplished, the valved sheath introducer is ready to be removed. In one embodiment, the handle is cracked by pulling a first side and a second side of the handle in opposite directions (i.e., away from the inserted medical device). This cracking action may take place, for example, along slots positioned in the handle between the first and second sides. By pulling the handle apart, the valve is separated such that one portion remains with the first side of the handle and another portion remains with the second side of the handle, as is described in exemplary embodiments herein. Once the handle is broken and the first and second sides are continued to be pulled in approximately opposite directions away from the inserted medical device, the sheath body is torn down its length so that complete removal of the valved sheath introducer from around the inserted medical device is possible without affecting the positioning of the medical device in the body vessel.

This invention has been described and specific examples of the invention have been portrayed. While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent covers those variations as well. Finally, all publications and patent applications cited in this specification are herein incorporated by reference in their entirety as if each individual publication or patent application were specifically and individually put forth herein.

What is claimed is:

1. A sheath introducer, comprising:
    a sheath body including a lumen;
    a handle attached to a proximal end of the sheath body, the handle including a bore communicating with the sheath body lumen, and at least a first receiving section and a second receiving section;
    a valve, comprising:
        a central portion disposed in the handle bore and including a cut portion;
        a first anchoring member received in the handle first receiving section;
        a second anchoring member received in the handle second receiving section; and
    a cap attached to the handle such that a portion of the valve is compressed between the cap and the handle, the valve exhibiting a bunching effect wherein the valve has a first shape prior to insertion of an instrument through the cut portion of the valve and a second shape different from the first shape after insertion of the instrument through, and removal of the instrument from, the cut portion of the valve.

2. The sheath introducer according to claim 1, wherein the second shape results from the valve stretching toward the instrument when inserted through the cut portion of the valve and being prevented from returning to the first shape upon removal of the instrument from the cut portion of the valve.

3. The sheath introducer according to claim 2, wherein the second shape includes a duckbill configuration at the central portion around the cut portion.

4. The sheath introducer according to claim 1, wherein the central portion of the valve has a thickness greater than a portion of the valve surrounding the central portion.

5. The sheath introducer according to claim 1, wherein the central portion has a concave surface on one side thereof.

6. The sheath introducer according to claim 5, wherein the central portion has opposing concave surfaces.

7. The sheath introducer according to claim 1, wherein the central portion has a diameter approximately equal to a diameter of the handle bore.

8. The sheath introducer according to claim 1, wherein the handle includes opposing slotted regions separating the first receiving section and the second receiving section.

9. The sheath introducer according to claim 8, wherein the cut portion is perpendicularly aligned with the opposing slotted regions.

10. The sheath introducer according to claim 9, further comprising a wire that is looped through the cut portion.

11. The sheath introducer according to claim 1, wherein the cut portion forms an acute angle with respect to a top surface of the valve.

12. The sheath introducer according to claim 1, wherein the valve further comprises at least one slit aligned with the cut portion.

13. The sheath introducer according to claim 12, wherein the at least one slit comprises a first slit positioned at a first edge of the valve and a second slit positioned at a second edge of the valve opposite the first slit.

14. The sheath introducer according to claim 13, wherein the handle includes opposing slotted regions separating the first receiving section and the second receiving section, and wherein the first slit and the second slit are aligned with the opposing slotted regions.

* * * * *